(12) United States Patent
Bansal et al.

(10) Patent No.: US 9,364,689 B2
(45) Date of Patent: Jun. 14, 2016

(54) COSMETIC COMPOSITIONS COMPRISING FIBROUS PIGMENTS

(75) Inventors: Amitabh Bansal, Hoboken, NJ (US); John R. Glynn, Jr., Ridgewood, NJ (US); Prithwiraj Maitra, Randolph, NJ (US)

(73) Assignee: Avon Products, Inc., New York, NY (US)

(*) Notice: Subject to any disclaimer, the term of this patent is extended or adjusted under 35 U.S.C. 154(b) by 289 days.

(21) Appl. No.: 12/645,067

(22) Filed: Dec. 22, 2009

(65) Prior Publication Data

US 2011/0150947 A1 Jun. 23, 2011

(51) Int. Cl.
 A61K 8/18 (2006.01)
 A61Q 1/02 (2006.01)
 A61K 8/02 (2006.01)
 A61K 8/29 (2006.01)

(52) U.S. Cl.
 CPC . A61Q 1/02 (2013.01); A61K 8/027 (2013.01); A61K 8/29 (2013.01); A61K 2800/437 (2013.01)

(58) Field of Classification Search
 CPC ... A61K 2800/437; A61K 8/027; A61K 8/29; A61Q 1/02
 USPC .................................................. 424/401, 63
 See application file for complete search history.

(56) References Cited

U.S. PATENT DOCUMENTS

| | | | |
|---|---|---|---|
| 5,763,497 A | 6/1998 | Ikeda et al. | |
| 6,511,672 B2 | 1/2003 | Tan et al. | |
| 7,531,184 B2 | 5/2009 | Horino et al. | |
| 2002/0028222 A1 | 3/2002 | Afriat | |
| 2002/0031533 A1 | 3/2002 | Afriat | |
| 2002/0192250 A1* | 12/2002 | Chevalier et al. | 424/401 |
| 2002/0197289 A1 | 12/2002 | Chevalier et al. | |
| 2003/0170306 A1 | 9/2003 | Raether et al. | |
| 2005/0191329 A1 | 9/2005 | Taniguchi | |
| 2007/0141095 A1 | 6/2007 | Simonnet | |
| 2007/0292459 A1 | 12/2007 | Cooper et al. | |
| 2008/0020207 A1 | 1/2008 | Hashiba et al. | |
| 2008/0207794 A1 | 8/2008 | Wright et al. | |
| 2009/0175915 A1 | 7/2009 | Maitra et al. | |

FOREIGN PATENT DOCUMENTS

| | | |
|---|---|---|
| EP | 0801941 B1 | 10/1997 |
| EP | 1951377 B1 | 8/2008 |
| JP | H04-297411 A | 10/1992 |
| JP | 08-048614 A | 2/1996 |
| JP | 09-104615 | 4/1997 |
| JP | 10-291922 A | 11/1998 |
| JP | 10291922 A * | 11/1998 |
| JP | 11-035441 A | 2/1999 |
| JP | 011035440 A | 2/1999 |
| JP | 02880084 B2 | 4/1999 |
| JP | 2003267815 | 9/2003 |
| JP | 2005-289932 A | 10/2005 |
| JP | 2007-039371 A | 2/2007 |
| JP | 2008-069125 A | 3/2008 |
| KR | 20030020000 A | 3/2003 |
| WO | 2007053647 A2 | 5/2007 |

OTHER PUBLICATIONS

Krishnaswamy, "BioSpec: A Biophysically-Based Spectral Model of Light Interaction with Human Skin" Thesis, Waterloo, Ontario, Canada, 2005 http://www.collectionscanada.ca/obj/s4/f2/dsk3/OWTU/TC-OWTU-538.pdf.

J. Y. Park and S. S. Kim, Metals and Materials International, vol. 15(1), pp. 95-99 (2009).

Drew et al. "Metal oxide coated polymer nanofibers," Nano Letters 2003, vol. 3, No. 2, pp, 143-147.

* cited by examiner

Primary Examiner — Sreeni Padmanabhan
Assistant Examiner — Courtney Brown
(74) Attorney, Agent, or Firm — David M. Joyal

(57) ABSTRACT

Cosmetic compositions comprising a fibrous pigment having an average diameter greater than 0.2 microns and an average aspect ratio greater than 5, and methods of using said compositions for imparting a pigmented film on skin or imparting a lightening appearance of skin are provided. The compositions optionally comprise from 0.1 to 30% of a coloring agent, selected from pigments, lakes, and dyes. The appearance of skin to which the compositions have been topically applied as a cosmetic film possesses L*, a*, and b* color space values and angular reflection properties closer to those of natural skin than an identical composition wherein the fibrous pigment has an average aspect ratio of less than 5.

17 Claims, 5 Drawing Sheets

COSMETIC COMPOSITIONS COMPRISING FIBROUS PIGMENTS

FIELD OF INVENTION

The present invention relates to methods of imparting cosmetic films on skin that are close to the reflection and color space profile of natural skin comprising topically applying a composition comprising fibrous pigments and coloring agents.

BACKGROUND

Pigments are often used in cosmetic compositions to hide imperfections in the skin, in particular skin discolorations. For hyperpigmentation, redness and shadows, pigments which can cover or lighten the appearance of skin are typically used. However, the use of pigments in cosmetic compositions can produce other aesthetic deficiencies. Each person's skin has certain angular reflectance and color space properties. These properties can change significantly in skin coated with a pigmented film or lightening composition and the result will appear unnatural. For example, pigments which provide a lighter appearance of the skin can also produce an ashy appearance on darker skin tones, which correlates with increasing angular dependence. Skin naturally has a close to Lambertian or flat reflection profile at incident angle of <60°.

Compositions that obscure blemishes by reflecting light away from them are known in the art. For example, compositions containing platelets of alumina treated with metal oxides and spherical scattering components comprised of silica coated with titanium dioxide are described in U.S. Pat. No. 6,511,672, which states that both components have intense reflection properties, rendering these pigments unsuitable for daytime wear if used alone because the intense reflection appears to enhance wrinkles and lines. Alternatively, pigment particles that have been coated with networks of smaller particles that have higher refractive indices can achieve a transparency that makes the skin look natural while hiding blemishes, as in U.S. Pat. No. 7,531,184. These compositions commonly employ titanium dioxide, which can produce an appearance of the skin that is too pearlescent or too chalky.

Titanium dioxide has often been mentioned in the art as causing cosmetic compositions to appear too white, powdery or chalky on skin. Fine particles of titanium dioxide are hard to disperse in cosmetic compositions and often form large aggregates. However, titanium dioxide particles having a larger size often become conspicuous in cosmetic compositions. European Patent No. 0801941 describes certain sunscreen compositions which employ spindle-shaped titanium dioxide rather than spherical shaped titanium dioxide to enhance the dispersion of the compound in the composition. It is stated in this patent that if the length or diameter of the spindle-shaped titanium becomes too long, the transparency in the visible light is detracted from, the finish of the sunscreen is diminished and the appearance of the skin becomes too white. Spindle- or needle-shaped titanium dioxide particles are also used in the cosmetic compositions of Japanese Patent Publication No. 11-035441, Japanese Patent No. 288084, Japanese Patent Publication No. 10-291922, Japanese Patent Publication No. 08-048614, and U.S. Pat. No. 5,763,497.

The need exists for alternative methods to lighten the appearance of skin, or to hide imperfections while maintaining a natural appearance of skin, which overcomes the problems associated with previous methods and compositions and which would represent a significant advance in cosmetic art.

The present invention provides methods for imparting a pigmented film by topical application of a cosmetic composition comprising certain fibrous pigments and coloring agents which are characterized in that the appearance of the skin is close to natural skin.

The present invention also provides methods for imparting a lightening appearance of skin by topical application of a cosmetic composition comprising certain fibrous pigments. None of the existing art provides the advantages and benefits of the present invention.

It is an object of the present invention to provide compositions comprising fibrous pigments that improve the appearance of skin while maintaining a reflection profile of the skin coated with the composition that is similar to natural skin.

It is another object of the present invention to provide compositions comprising fibrous pigments that improve the appearance of skin while maintaining color space values of the skin coated with the composition that are similar to natural skin.

SUMMARY OF THE INVENTION

In accordance with the foregoing objectives and others, the present invention provides methods of imparting pigmented films that are close to the reflection and color space profile of natural skin comprising topically applying a composition comprising fibrous pigments and coloring agents In another aspect, the present invention provides methods for imparting a soft focus effect, lightened appearance or whitening effect of skin comprising topically applying a composition comprising fibrous pigments.

Methods of imparting a pigmented film on skin comprising topically applying a composition comprising 0.1 to 30% by weight of a fibrous pigment having an average diameter greater than 0.2 microns and an average aspect ratio greater than 5 and from 0.1 to 30% of a coloring agent, selected from pigments, lakes, and dyes are provided. In one embodiment, the pigmented film on said skin is characterized in that the appearance of the skin is more natural than a film provided by an otherwise identical composition wherein the fibrous pigment has an average aspect ratio of less than 5. In one embodiment, the composition provides a soft focus effect.

Methods of imparting a lightening appearance of skin comprising topically applying a composition comprising 0.1 to 30% by weight of a fibrous pigment having an average diameter greater than 0.2 microns and an average aspect ratio greater than 5 are provided.

In one embodiment, the cosmetic film or pigmented film on the skin is characterized by substantially Lambertian reflection.

In one aspect, the fibrous pigment comprises a metal oxide, for example $TiO_2$, Halloysite, ZnO, or an iron oxide. In certain embodiments, the fibrous pigment has an average diameter of 0.25 to 1.5 micron and an average aspect ratio greater than 10. The fibrous pigments can be in the form of solid fibers, hollow fibers, for example Halloysite fibers, fibers with asperities, or fibers comprised of a polymeric material and coated with metal oxides.

In one embodiment, the composition further comprises one or more depigmentation agents or may be used in combination with one or more depigmentation agents or composition comprising one or more depigmentation agents.

In one embodiment, the composition is characterized by a diffuse transmittance of at least 35 and reflectance value of less than 30 on a 0.3 mils thick film. The composition may comprise soft focus materials, for example cellulose beads. In certain embodiments, the ratio of the weight of the soft focus materials to the weight of the fibrous pigment in the range of 3:1 to 1:3. In one embodiment, the soft focus materials and fibrous pigment each comprise 1 to 20% of the composition by weight.

In certain embodiments, the composition is free of iron-containing pigment, colored pigment, or sunscreen agents.

In one aspect, the methods of imparting a pigmented film on skin comprising topically applying a composition as described herein to provide a pigmented film on said skin, wherein the pigmented film on the skin is characterized in that the appearance of the skin as measured in the L*, a* and b* color space values is closer to that of natural skin than the L*, a* and b* color space values of an identical composition wherein the fibrous pigment has an average aspect ratio of less than 5.

In another aspect, the methods of imparting a lightening appearance of skin comprising topically applying a composition as described herein provide a cosmetic film on said skin, wherein the cosmetic film on the skin is characterized in that the appearance of the skin as measured in the L*, a* and b* color space values is closer to that of natural skin than the L*, a* and b* color space values of an identical composition wherein the fibrous pigment has an average aspect ratio of less than 5.

In certain embodiments, the sum of the difference in L*, a* and b* color space values of the composition comprising a fibrous pigment having an average aspect ratio greater than 5 as compared to that of natural skin is less than the sum of the difference in L*, a* and b* color space values of the composition comprising a fibrous pigment having an average aspect ratio less than 5 as compared to that of natural skin.

These novel features of the present invention will become apparent to those skilled in the art from the following detailed description, which is simply, by way of illustration, various modes contemplated for carrying out the invention. As will be realized, the invention is capable of additional, different obvious aspects, all without departing from the invention. Accordingly, the specification is illustrative in nature and not restrictive.

DETAILED DESCRIPTION OF THE INVENTION

Figure 1:
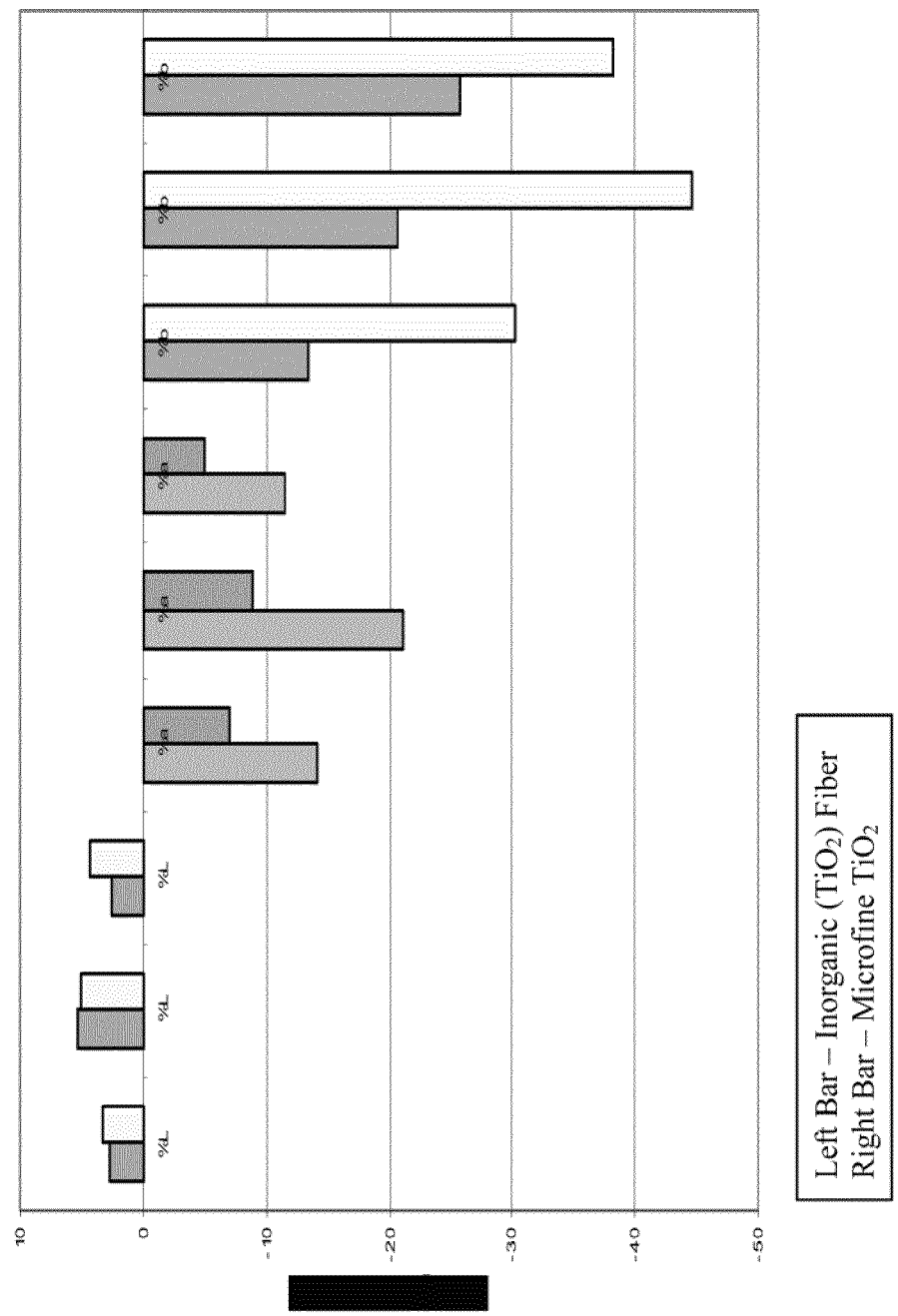
FIG. 1 shows the change in CIELAB L*, a* and b* values of Velvasil base 7-4 drawdowns of 5% by weight $TiO_2$ fiber compared to 5% by weight spherical microfine $TiO_2$.

By "fiber" is meant is a class of materials that are continuous filaments or are in discrete elongated pieces, similar to lengths of thread. Fibers can be solid, hollow, dimpled, covered with asperities or coated.

The term "pigment" refers to a material that changes the color of reflected or transmitted light. Pigments can be inorganic or organic. Pigments of the present invention can be in the form of a fiber or coated polymeric fiber.

The phrase "cosmetically acceptable vehicle" refers to a medium that is compatible with keratin materials, such as human skin.

For the purposes of the invention, the term "polymer" means a compound containing at least two repeating units, such as, for example, a compound containing at least three repeating units, which may be identical.

The term "dispersal" as used herein refers to any process by which the ingredients are uniformly distributed in the emulsified base, and includes dissolving, emulsifying, and forming a colloidal suspension or gel.

As used herein the term "effective amount" refers to an amount sufficient to result in a lightening, whitening or soft focus appearance of the skin.

The terms "a" and "an", as used herein and in the appended claims, mean "one or more" unless otherwise indicated herein.

It should be noted that unless indicated to the contrary, as used herein, percent (%) is % by weight, based on the total weight of the composition.

Fibrous Pigments

The fibrous pigments for use in the present invention can be comprised of organic substances, inorganic substances of mixtures thereof. The fibrous pigments may take the form of a coated polymeric fiber.

"Metal oxide" as used herein refers to a compound which comprises at least one oxygen atom and at least one metal atom. The inorganic fibrous pigments or inorganic fibers for use in the present invention comprise a metal oxide, included but not limited to titania, for example titanium dioxide ($TiO_2$); iron oxides, for example FeO and $Fe_2O_3$; alumina or aluminum oxides, for example $Al_2O_3$; zinc oxide (ZnO), and silica ($SiO_2$). The fibrous pigments can be used alone or in combination with other fibrous pigments, for example mixtures of metal oxides. In one embodiment, the inorganic fibrous pigments can comprise one or more inorganic fibrous pigments. In certain embodiments, the fibrous pigments comprise metal oxides which are comprised of at least one oxygen atom and at least one transition metal atom, for example titanium vanadium, chromium, manganese, iron, cobalt, nickel, copper, and zinc. In another embodiment, the fibrous pigments comprise metal oxides which are comprised of at least one oxygen atom and at least one aluminum atom. In one embodiment, the fibrous pigment is $TiO_2$. In another embodiment, the fibrous pigment is $SiO_2$. In certain embodiments, the fibrous pigment comprises $TiO_2$ and $Al_2O_3$; $TiO_2$ and $SiO_2$; or $TiO_2$ and $Fe_2O_3$.

In one embodiment, the fibrous pigment is a manmade or synthetic substance. In another embodiment the fibrous pigment is a naturally occurring substance.

In another aspect, the fibrous pigment comprises a clay mineral compound or aluminasilicate including but not limited to Halloysite ($Al_2Si_2O_5(OH)_4$; Kaolinite); Illite—(K, $H_3O)(Al,Mg,Fe)_2(Si,Al)_4O_{10}[(OH)_2,(H_2O)]$; Montmorillonite—$(Na,Ca)_{0.33}(Al,Mg)_2(Si_4O_{10})(OH)_2 \cdot nH_2O$; Vermiculite—$(MgFe,Al)_3(Al,Si)_4O_{10}(OH)_2 \cdot 4H_2O$; Talc—$Mg_3Si_4O_{10}(OH)_2$; Palygorskite—$(Mg,Al)_2Si_4O_{10}(OH) \cdot 4(H_2O)$; and Pyrophyllite—$Al_2Si_4O_{10}(OH)_2$; silicate, or other mineral derived tubule. In another preferred embodiment, the fibrous pigment is Halloysite. In certain embodiments, the clay mineral compound is a metal oxide, as defined herein.

In one aspect the fibrous pigments comprise an organic substance, for example carbon fiber or carbon nanotubes.

The fibers or fibrous pigments can be solid or hollow and can further be covered with dimples or asperities. In one embodiment, the fibers are solid. In another embodiment, the fiber is hollow. In one embodiment, the fiber is solid or hollow and is covered with dimples or asperities.

In certain embodiments, the fiber is solid, needle-shaped, spindle-shaped, rugby-shaped, football-shaped or rod-shaped. In certain embodiments, the fibrous pigment is cylindrical. In a particular embodiment, the fibrous pigment is solid $TiO_2$, for example solid $TiO_2$ nanofiber prepared by electrospinning methods (see for example J. Y. Park and S. S. Kim, *Metals and Materials International*, Vol 15(1), pp. 95-99 (2009)).

In other embodiments, the fibrous pigment is hollow or in the shape of a tube. In a preferred embodiment the fibrous pigment is Halloysite, which is hollow or tube-shaped. In subembodiments, the hollow fiber is filled with one or more substances which may provide additional benefits to the skin, for example moisturizing compounds such as glycerine.

The fibrous pigment can be deposited as a coating on any polymeric material. The polymeric material, which can take the form of a solid or hollow fiber, is coated with fibrous pigments, inorganic fibers, metal oxides or clay mineral compounds, and can be described as core-sheath fibers. The fibrous pigments, inorganic fibers, metal oxides or clay mineral compounds, can be deposited onto the polymeric material or polymeric fiber by known methods described in the literature (see for example Drew et al. "Metal oxide coated polymer nanofibers," *Nano Letters* 2003, Vol. 3, No. 2, pp, 143-147). Such core-sheath fibers can be advantageous for reducing the cost of the materials without compromising the desirable properties imparted by the fibrous pigments or inorganic compounds.

The polymeric material is not restricted to any particular type or types of polymers. In certain embodiments, the polymeric material comprises polyamides, for example Nylon, Polyacrylic acid (PAA), Cross-linked polyethylene (PEX or XLPE), Polyethylene (PE), Polyethylene terephthalate (PET or PETE), Polyphenyl ether (PPE), Polyvinyl chloride (PVC), Polyvinylidene chloride (PVDC), Polylactic acid (PLA), Polypropylene (PP), Polybutylene (PB), Polybutylene terephthalate (PBT), Polyamide (PA), Polyimide (PI), Polycarbonate (PC), Polytetrafluoroethylene (PTFE), Polystyrene (PS), Polyurethane (PU), Polyester (PEs), Acrylonitrile butadiene styrene (ABS), Polymethyl methacrylate (PMMA), Polyoxymethylene (POM), Polysulfone (PES), Styrene-acrylonitrile (SAN), Ethylene vinyl acetate (EVA), Styrene maleic anhydride (SMA) and polyacrylonitrile; or polyvinyl alcohol (PVA). In preferred embodiments, the polymeric material is selected form the group consisting of Nylon, polyacrylonitrile, PVA and PMMA.

In one embodiment, the polymeric material is coated with a metal oxide. In a particular subembodiment, the metal oxide is $TiO_2$. In another embodiment, the polymeric material is coated with a clay mineral compound. In a particular subembodiment, the clay mineral compound is Halloysite.

The polymeric fibers have an average diameter 0.05 microns or greater and an average aspect ratio of 5 or greater. In certain embodiments, the polymeric fibers have an average diameter 0.05 to 20 microns and an average aspect ratio 5 or greater. The coating on the polymeric fiber may be continuous layer of an average thickness of about 0.01 to 20 microns. The coating may be discontinuous or consist of distinct particles in the size range of 0.005 to 20 microns. The coating may also consist of fiber, plate or spherical shaped particles.

In another aspect, the fibrous pigment can impart a desired color, or a lightening or whitening appearance to the skin. In subembodiments, the fibrous pigment is $TiO_2$, Halloysite or iron oxide. In preferred embodiments, the fibrous pigment imparts a lightening or whitening appearance to the skin, for example as used in a cream, lotion, foundation, eye cream or other composition for topical application to facial skin. In a preferred embodiment, the fibrous pigment is used as a coating on a polymeric material to impart a desired color to the skin, for example as used in a foundation or eye shadow.

The average diameter and average aspect ration of the fibrous pigments used in the compositions described herein affects the color of the composition. Fibrous pigment which have L*, a* and b* color space values to that of natural skin are preferred for the compositions of the present invention. Certain fibrous pigments, for example fibrous pigments with average diameters smaller than about 0.2 microns, with average aspect ratios less than 5, for example spherical pigments, are not useful in the methods described herein. For example, $TiO_2$ with a diameter smaller than about 0.2 microns imparts a blue color or bluish appearance when applied to the skin in a composition. In a particular aspect, the fibrous pigment has an average diameter greater than 0.2 microns. In certain embodiments, the fibrous pigment has an average diameter greater than about 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.50 or 0.60 microns. In preferred embodiments, the fibrous pigment has an average diameter greater than 0.26 microns.

In certain embodiments, the fibrous pigment has an average diameter of about 0.2 to 1.5, 0.2 to 1.0, 0.2 to 0.8, 0.2 to 0.7, 0.2 to 0.6, 0.2 to 0.5, 0.2 to 0.4, 0.2 to 0.3, 0.21 to 0.50, 0.25 to 0.50, 0.26 to 0.50, 0.27 to 0.50, 0.28 to 0.50, 0.21 to 0.40, 0.25 to 0.40, 0.26 to 0.40, 0.27 to 0.40, 0.28 to 0.40, 0.21 to 0.35, 0.26 to 0.35, 0.27 to 0.35, 0.21 to 0.32, 0.26 to 0.31 or 0.27 to 0.31 microns. In a particular embodiment, the fibrous pigment has a diameter in the range of about 0.21 to 0.50 microns.

The length of the fibrous pigment is greater than the diameter of the fiber but is otherwise not particularly limited. In certain embodiments, the average length of the fibrous pigment is greater than about 0.25, 0.30, 0.35, 0.40, 0.50, 0.75, 1, 2, 3, 4, 5, or 10 microns. In a preferred embodiment, the average length of the fibrous pigment is greater than 1 micron.

In other embodiments, the average length of the fiber can be in the range of about 0.25 to 100, 0.30 to 100, 1 to 100, 5 to 100, 0.25 to 50, 0.30 to 50, 1 to 50, 5 to 50, 0.25 to 30, 0.30 to 30, 1 to 30, 5 to 30, 0.25 to 20, 0.30 to 20, 1 to 20, 5 to 20, 0.25 to 10, 0.30 to 10, 1 to 10, or 5 to 10 microns. In a preferred embodiment, the average length of the fibrous pigment is about 1 to 20 microns.

The average aspect ratio of the fibrous pigment is the ratio of its longer dimension to its shorter dimension, or the value obtained when the length is divided by the diameter. Preferred fibrous pigment of this invention have a high aspect ratio or an aspect ratio that would improve optical properties of skin. In certain embodiments, the average aspect ratio of the fibrous pigment is greater than 1, 2, 3, 4, 5, 10, 20, 30, 40, 50, or 100.

In one embodiment, the average aspect ratio of the fibrous pigment or fiber is greater than 5. In another embodiment, the average aspect ratio of the fibrous pigment is greater than 10.

In other embodiments, the average aspect ratio of the fibrous pigments is in the range of about 1 to 1000, 2 to 100, 3 to 100, 4 to 100, 5 to 100, 10 to 100, 20 to 100, 30 to 100, 40 to 100, 50 to 100, 1 to 20, 2 to 20, 3 to 20, 4 to 20, 5 to 20, 5 to 30, 5 to 50, to 20, 10 to 30, or 10 to 50. In one embodiment, the average aspect ratio of the fibrous pigments is in the range of about 1 to 100, more preferably 5 to 100. The fibers are not spherical.

In another aspect, the average refractive index of the fibrous pigments is in the range of about 1.01 to 4.0, 2.0 to 4.0, 1.1 to 3.5, 1.7 to 3.5, 2.0 to 3.5, 1.5 to 3.2, 1.7 to 3.2, 2.0 to 3.2, or 2.0 to 3.0. In a preferred embodiment, the average refractive index of the fibrous pigments is in the range of about 2.0 to 3.0.

Compositions

Compositions comprising the fibrous pigments described herein can be used to impart a soft focus effect, lightened appearance or whitening effect to the skin. In certain embodiments, the composition further comprises a coloring agent, selected from pigments, lakes, and dyes. Particularly preferred compositions are compositions that can be applied to the face, neck, chest, arms or hands. The type of composition is not particularly limited and any formulation suitable for application to human skin, or any cosmetic formulation, can be used. In certain embodiments, the compositions can be a powder, cream, lotion, gel, emulsion, moisturizer, foundation, concealor or other cosmetic compositions or vehicles. In certain embodiments, the compositions are applied to all or part of the face, for example around the eye, under the eye or a part of the face afflicted with blemishes, hyperpigmentation, uneven skin tone or other discoloration. In certain embodiments, the composition is applied to the hands. In a particular embodiment, the composition is applied to a patch of skin afflicted with hyperpigmentation or other discoloration. In certain embodiments, the composition is not a powder.

The compositions may comprise about 0.1% to 50%, 0.5% to 40%, 0.1% to 30%, 1% to 30%, 2% to 30%, 1% to 20%, 2% to 20%, 2% to 15%, 2% to 10%, 2% to 5%, 5% to 20%, 5% to 15%, relative to the total weight of the composition, of one or more types of the fibrous pigments. In a preferred embodiment, the composition comprises about 2% to 20% by weight of the fibrous pigments.

In a preferred embodiment, the composition is for whitening or lightening the appearance of skin and comprises 2-6% by weight of the fibrous pigments. In another preferred embodiment, the composition is a foundation and comprises 5-20% by weight of the fibrous pigments.

In one aspect, the composition comprises one or more soft focus materials. In one embodiment, the soft focus material is a cellulose bead. The compositions can include a spherical scattering component comprising spherical powders that achieve a soft focus look such as calcium aluminum borosilicate, PMMA, polyethylene, polystyrene, methyl methacrylate crosspolymer, nylon-12, ethylene/acrylic acid copolymer, boron nitride, Teflon, silica, or the like.

The compositions may comprise about 0.1% to 50%, 0.5% to 40%, 0.1% to 30%, 1% to 30%, 2% to 30%, 1% to 20%, 2% to 20%, 2% to 15%, 2% to 10%, 2% to 5%, 5% to 20%, 5% to 15%, relative to the total weight of the composition, of soft focus materials. In a preferred embodiment, the composition comprises about 2% to about 20% by weight soft focus materials.

In certain embodiments, the ratio of the weight of the soft focus materials to the weight of the fibrous pigments in the range of about 50:1 to 1:50, 20:1 to 1:20, 10:1 to 1:10, 5:1 to 1:5, 3:1 to 1:3, 2:1 to 1:2 or 1:1. In a preferred embodiment, the ratio of the weight of the soft focus materials to the weight of the fibrous pigments in the range of about 3:1 to 1:3. In another preferred embodiment, the ratio of the weight of the soft focus materials to the weight of the fibrous pigments is about 1:1.

In other embodiments, the combined % by weight of inorganic fibers and soft focus materials in the composition is about 0.1% to 50%, 0.5% to 40%, 0.1% to 30%, 1% to 30%, 2% to 30%, 1% to 20%, 2% to 20%, 2% to 15%, 2% to 10%, 2% to 5%, 5% to 20%, 5% to 15%, relative to the total weight of the composition.

The composition of the invention may also be in the form of a colored make-up product for the skin, such as a foundation or concealor produce, a face powder, a serum, a top or bottom make-up coat, a make-up product for the body; a make-up product for the lips such as a lipstick; or pencil, all of which may optionally having care or treating properties. In a preferred embodiment, the composition is a foundation.

In a particular embodiment, the composition is a colored make-up composition, for example a foundation. In one embodiments, the colored make-up composition provides a high level of coverage while maintaining angular reflectance properties and color space values close to that of natural skin.

Colored cosmetics will typically comprise one or more coloring agents selected from pigments, lakes, and dyes. The additional coloring agents, if present, will typically comprise from about 0.1% to about 30% by weight of the composition, and more typically from about 0.1% to about 10% by weight of the composition. In certain embodiments, the coloring agent is iron oxide.

Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Non-metal oxides such as alumina and silica, ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like, are also contemplated to be suitable inorganic pigments. Organic pigments can include, but are not limited to, at least one of carbon black, carmine, phthalocyanine blue and green pigment, diarylide yellow and orange pigments, and azo-type red and yellow pigments such as toluidine red, litho red, naphthol red and brown pigments, and combinations thereof.

Lakes generally refer to a colorant prepared from a water-soluble organic dye, (e.g., D&C or FD&C) which has been precipitated onto an insoluble reactive or adsorptive substratum or diluent. The term "D&C" means drug and cosmetic colorants that are approved for use in drugs and cosmetics by the FDA. The term "FD&C" means food, drug, and cosmetic colorants which are approved for use in foods, drugs, and cosmetics by the FDA. Certified D&C and FD&C colorants are listed in 21 C.F.R. §74.101 et seq. and include the FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Substrates suitable for forming lakes include, without limitation, mica, bismuth oxychloride, sericite, alumina, aluminum, copper, bronze, silver, calcium, zirconium, barium, and strontium, titanated mica, fumed silica, spherical silica, polymethylmethacrylate (PMMA), micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof. Suitable lakes include, without limitation, those of red dyes from the monoazo, disazo, fluoran, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof, such as Yellow 5, 6, 7, 8, 10, and 11; lakes of violet dyes including those from the anthroquinone family, such as Violet 2. as well as lakes of orange dyes, including Orange 4, 5, 10, 11, and the like. Suitable Lakes of D&C and FD&C dyes are defined in 21 C.F.R. §82.51.

The coloring agents may be optionally surface treated, for example, to make the particles more hydrophobic or more dispersible in a vehicle. The surface of the particles may, for example, be covalently or ionically bound to an organic molecule or silicon-based molecule or may be adsorbed thereto, or the particle may be physically coated with a layer of material. The surface treatment compound may be attached to the particle through any suitable coupling agent, linker group, or functional group (e.g., silane, ester, ether, etc). The compound may comprise a hydrophobic portion which may be selected from, for example, alkyl, aryl, allyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include lauroyl lysine, Isopropyl Titanium Triisostearate (ITT), ITT and Dimethicone (ITT/Dimethicone) cross-polymers, ITT and Amino Acid, ITT/Triethoxycaprylylsilane Crosspolymer, waxes (e.g., carnauba), fatty acids (e.g., stearates), HDI/Trimethylol Hexylactone Crosspolymer, PEG-8 Methyl. Ether Triethoxysilane, aloe, jojoba ester, lecithin, Perfluoroalcohol Phosphate, and Magesium Myristate (MM), to name a few.

In some embodiments, an optional pigment component includes and alkyl silane surface-treated colorant consisting essentially of or comprising an alumina substrate (e.g., platelet shaped) and a pigment, dye, or lake bonded to the alumina substrate by an alkyl silane surface treatment. Typically, the alkyl silane will be octylsilane and may be formed by treatment with Triethoxy Caprylylsilane. Nonlimiting examples of such colorants include, but are not limited to, A lumina/Titanium Dioxide/Triethoxycaprylylsilane 1% (COVALUMINE™ Atlas White AS), Alumina/D&C Red Aluminum Lake CTD/Triethoxycaprylylsilane 1% (COVALUMINE™ Red Rose AS), Alumina/D&C Red Aluminum Lake CTD/Triethoxycaprylylsilane 1% (COVALUMINE™ Sonoma Red AS), Alumina/Black Iron Oxide CTD/Triethoxycaprylylsilane 1% (COVALUMINE™ Sonoma Black AS), Alumina/D&C Red #6 Aluminum Lake CTD/Triethoxycaprylylsilane 1% (COVALUMINE™ Fire Red AS), Alumina/Yellow Iron Oxide CTD/Triethoxycaprylylsilane 1% (COVALUMINE™ Sonoma Yellow AS), Alumina/D&C Blue #1 Aluminum Lake CTD/Triethoxycaprylylsilane 1% (COVALUMINE™ Astral Blue AS), Alumina/Carmine CTD/Triethoxycaprylylsilane 1% (COVALUMINE™ Campari AS), Alumina/Yellow #5 CTD/Triethoxycaprylylsilane 1% (COVALUMINE™ Sunburst AS), Alumina/Triethoxycaprylylsilane 1%, and combinations thereof, each of which is available from SENSIENT™ Cosmetic Techologies LCW.

Interference or pearl pigments may also be included. These are typically comprised of micas layered with about 50 to 300 nm films of $TiO_2$, $Fe_2O_3$, or $Cr_2O_3$ or the like. These include white nacreous materials, such as mica covered with titanium oxide or covered with bismuth oxychloride; and colored nacreous materials, such as titanium mica with iron oxides, titanium mica with ferric blue or chromium oxide, titanium mica with an organic pigment of the aforementioned type. However, these other materials sometimes lend a white, chalky, ashy appearance to the skin when the final composition is applied to the skin, and thus these materials are preferably not used in the present invention or their amount should be limited. If they are used, it is preferred that these materials are used collectively in an amount of less than 1.0 wt %. Preferably, the pearlescent component has a bismuth oxychloride based pearlescent ingredient or reflectance pearls. Bismuth oxychloride matches the skin's natural pearlescence more than compounds such as titanium oxide, which provide for a more artificial look. Bismuth oxychloride better mimics the skin's natural reflectance. However, other pearlescent ingredients may be used. A preferred pearlescent component is called CHROMA-LITE, which is a combination of colored pigment bonded to BI-LITE 20 (bismuth oxychloride and mica) using calcium stearate. The CHROMA-LITE component is available in various shades/color from Englehard Corporation (Iselin, N.J.).

The composition of the invention should be cosmetically or dermatologically acceptable, i.e., it should contain a non-toxic physiologically acceptable medium and should be able to be applied to the skin, superficial body growths or the lips of human beings. For the purposes of the invention, the expression "cosmetically acceptable" means a composition of pleasant appearance, odor, feel and taste.

In one embodiment, the composition is a face cream or eye cream for whitening, brightening or lightening the appearance of skin.

In a particular embodiment, the composition is not a cleanser. In other embodiments, the composition does not absorb sebum. In certain embodiments, the composition is not a scrub, for example a scrub that removes keratin, or a mask or pack, for example a peel-off mask.

In one embodiment, the composition comprises one or more pigments selected to achieve a range in color or shade. In certain embodiments, the compositions can be formulated to achieve a broad range in color or shade. In particular embodiments, the range in color or shade is improved or broadened over the prior art.

The composition can be formulated as a foundation or concealor, for example, liquids, gels, creams, lotions, moisturizers, tinted moisturizers, cakes, sticks, pans, powders and not limited to any particular type of foundation or concealor. Any physiologically acceptable medium can form the base of the composition. The term "physiologically acceptable medium" means a medium which is compatible with the skin, the mucous membranes and/or the integuments thereof. In one aspect of the invention, the composition comprises other coloring agents or pigments. In certain embodiments, the composition is a foundation, tinted moisturizer, or concealer. In other embodiments, the composition is a cream or powder eye shadow composition. In certain embodiments, the composition is not an eye shadow composition. In certain embodiments, the composition do not comprise additional coloring agents or pigments. In one embodiment, the composition does not comprise iron-containing pigments, for example iron oxide.

In one embodiment, the composition comprises one or more sunscreen agents. In certain embodiment, the fibrous pigment is a UV blocking agent. In certain embodiments, the composition does not contain sunscreens, sunscreen agents or UV blocking agents. In one embodiment, the fibrous pigment or coating on the polymeric fiber is not comprised of a sunscreen, sunscreen agent or UV blocking agent.

All ingredients useful herein may be categorized or described by their postulated mode of action. However, it is to be understood that the ingredients can, in some instances, provide more than one cosmetic and/or therapeutic benefit or operate via more than one mode of action. Therefore, classifications herein are made for the sake of convenience and are not intended to limit an ingredient to the particularly stated application or applications listed.

The composition of the present invention may also include other cosmetic ingredients such as, but not limited to, humectants, emollients, moisturizers, anti-wrinkle ingredients, concealors, matte finishing agents, pigments, colorants, proteins, anti-oxidants, bronzers, chelating agents, emulsifiers, ultraviolet (UV) absorbing agents, oil absorbing agents, anti-foam agents, anti-tack agents, thickeners, fragrances, preservatives, anti-microbials, fungistats, neutralizing agents, vitamins, plasticizers, cohesion agents, basifying and acidifying agents, fillers, solvents, and mixtures thereof. It is understood to those skilled in the art that any other cosmetically acceptable ingredient, i.e., those included in the CFTA Cosmetic Ingredient Dictionary, 3rd ed. may be used.

The compositions may contain additional ingredients such as alkalinizing agents, emulsifying agents, emollients, plasticizers, preservatives, humectants, moisturizing agents, solvents, and tonicity agents or active ingredients suitable to provide anti-aging benefits. Examples of preferred additional ingredients include glycerin. Viscosifying agents such as gellants may also be used. Examples include, bentone, triglycerides, aluminum stearate, C18-C36 acid glycol esters, glyceryl tribehenate, glycerol monostearate, alginates, carbomers, celluloses, gums, carageenans, starches or silicates. Fillers can also optionally be added, in an amount from about 1% to about 20%, preferably from about 1% to about 10%. Examples of fillers include silica, PMMA, nylon, alumina, barium sulfate, or any other filler typically used in such compositions.

The composition may also contain at least one cosmetic active ingredient and/or at least one dermatological active ingredient, i.e. an agent having a beneficial effect on the skin. The loading of such active ingredient can be achieved in any means known to those skilled in the art. The composition may comprise further comprise other whitening or lightening agents that either hide the discoloration with pigments or other light-reflecting materials, or treat the cause of the discoloration.

In a particular embodiment, the compositions may comprise one or more depigmentation agents or may be used in combination or alternation with one or more depigmentation agents. A depigmentation agent is any active agent having skin-depigmenting activity. This activity makes it possible to decrease the pigmentation of the skin that already exists and also to prevent any additional pigmentation above the natural pigmentation. Depigmentation agents include but are not limited to tyrosinase inhibitors, Thiodiproionic acid (TDPA) and derivatives thereof, bearberry extract, phytol, mangosteen, hydroquinone and derivatives thereof, azelaic acid and derivatives thereof, kojic acid (5-hydroxy-4-pyran-4-one-2-methyl) and derivatives thereof, mequinol (4-hydroxyanisole), retinoids, niacinamide, serine protease inhibitors, soy or soy extract, alpha hydroxy acids, glycolic acid, trichloroacetic acid, salicylic acid, arbutin (hydroquinone-beta-D-glucopyranoside), paper mulberry, glabridin (licorice extract), arctostaphylos patula, arctostaphylos viscida, magnesium ascorbyl phosphate, 4-isopropylcatechol, aleosin, phenolic thioethers, for example N-acetyl-4-S-cysteaminylphenol or N-propionyl-4-S-cysteaminylphenol, N-acetyl glucosamine, tranexamic acid (trans-4-aminomethylcyclohexanecarboxylic acid), linoleic acid, resorcinol and derivatives thereof, ellagic acid, ascorbic acid, zinc peroxide, and other depigmentation or skin-lightening agents known in the art. The compositions may comprise from 0.0001% to 20% by weight of depigmenting agent relative to the total weight of the composition, and preferably, from 0.025% to 5% by weight of depigmenting agent relative to the total weight of the composition.

It is also possible to employ a controlled release type of active ingredient delivery system. In this respect it also can be achieved that the active ingredient is released over a short period of time, which is desired in some fields of application. In particular, the hollow inorganic fiber may hold or encapsulate the active ingredient to be released. Such ingredients may include active agents, such as vitamins, skin care agents, anti-inflammatory agents, for example steroidal or non-steroidal anti-inflammatory agents, or other agents which are known in the field of cosmetic preparations.

A person skilled in the art will take care to select the optional additives and/or the amount thereof such that the advantageous properties of the composition according to the invention are not, or are not substantially, adversely affected by the envisaged addition. It is further understood that the other cosmetic ingredients and adjuvants introduced into the composition must be of a kind and quantity that are not detrimental to the advantageous effect which is sought herein according to the invention.

The composition may comprise film formers or film-forming agents. Film-forming agents include PVP, acrylates, acrylamides, copolymers, organosiloxanes, including polydimethylsiloxane (PDMS or Dimethicone), silicone polyurethane, polyorganosiloxane polyurethane polymer, or other film forming agents known in the art. Film formers improves the ability of the compositions to leave a pliable, cohesive, and continuous covering over the skin. The film may have water-binding properties and leaves a smooth feel on skin.

The compositions may comprise about 1% to 90%, 2% to 80%, 5% to 85%, 10% to 80%, 20% to 70%, 30% to 60%, 40% to 60%, relative to the weight of the total composition, of water. Generally, the amount of water present in the composition of the invention is at least about 20%.

Methods of Use

The compositions comprising the fibrous pigments described above are designed to impart a pigmented film on skin characterized in that the appearance of the skin is more natural than a film provided by an otherwise identical composition wherein the fibrous pigment has an average aspect ratio of less than 5. In certain embodiments, the compositions provide pigmented films or cosmetic films on skin that have angular reflection profiles or color space values close to that of natural skin.

In another aspect, the compositions provide a lightening or whitening effect to skin and an angular reflection profile that is close to that of natural skin or is characterized by a substantially Lambertian profile. Skin has a more Lambertian reflection profile at incident angles of less than 60°. The lightening or whitening effect of many compositions can produce an ashy or grayish appearance of the skin. The ashy appearance of materials is characterized by the angular reflection of light. In particular, the greater the angular dependence, the more ashy the material looks.

If a surface exhibits Lambertian reflectance, light falling on it is scattered such that the apparent brightness of the surface to an observer is the same regardless of the observer's angle of view. More specifically, the surface luminance is isotropic. A substantially Lambertian profile or substantially Lambertian reflection refers to surface luminance that is substantially isotropic or is approximately the same regardless of the observer's angle of view.

Lambertian reflection is often used as a model for diffuse reflection. Diffuse reflection is the reflection of light from an uneven or granular surface such that an incident ray is seemingly reflected at a number of angles. It is the complement to specular reflection. If a surface is completely nonspecular, the reflected light will be evenly spread over the hemisphere surrounding the surface. Specular reflection, where the surface luminance is highest when the observer is situated at the perfect reflection direction, and falls off sharply.

In another aspect, the methods of imparting a lightening appearance of skin provide a cosmetic film on said skin, wherein the cosmetic film on the skin is characterized in that the appearance of the skin as measured in the L*, a* and b* color space values is closer to that of natural skin than the L*, a* and b* color space values of an identical composition wherein the fibrous pigment has an average aspect ratio of less than 5.

"Lab color space" refers to a color-opponent space with dimension L for lightness and a and b for the color-opponent dimensions, based on nonlinearly compressed CIE XYZ color space coordinates. The coordinates of the Hunter 1948 L, a, b color space are L, a, and b. Lab is now commonly used as an informal abbreviation for the CIE 1976 (L*, a*, b*) color space (also called CIELAB). As used herein, the initials L, a, b, or L*, a*, b*, refer to CIELAB color space values.

The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

In certain embodiments, the sum of the difference in L*, a* and b* color space values of the composition comprising a fibrous pigment having an average aspect ratio greater than 5 as compared to that of natural skin is less than the sum of the difference in L*, a* and b* color space values of the composition comprising a fibrous pigment having an average aspect ratio less than 5 as compared to that of natural skin.

In one aspect, a method of imparting a lightening appearance of skin comprising topically applying a composition comprising 0.1 to 50%, by weight of a fibrous pigment having an average diameter greater than 0.2 microns and an average aspect ratio greater than 1, to provide a cosmetic film on said skin characterized by substantially Lambertian reflection.

In a preferred embodiment of any of the compositions described herein, the composition comprises 0.1 to 30%, or more preferably, 2 to 20%, by weight of a fibrous pigment. In another preferred embodiment, the fibrous pigment has an average diameter greater than 0.26 microns. In another preferred embodiment, the fibrous pigment has an average aspect ratio greater than 5 or 10.

In one embodiment, the substantially Lambertian reflection refers to the minimal difference in L* across a range of −20° to 130° from specular and the incident light is at an angle of less than 60°. In particular embodiment, the difference in L* across a range of −20° to 130° from specular and the incident light is at an angle of less than 60° is less than 10%, or more preferably 6%.

In certain embodiments, the fibrous pigment comprises one or more types of inorganic fibers, for example one or more metal oxides, one or more clay mineral compounds, or a mixture thereof. In one embodiment, the inorganic fiber is titania or Halloysite.

In one embodiment, the fibrous pigment is solid. In another embodiment, the fibrous pigment is hollow. In certain embodiments, the fibrous pigment is a mixture of solid and hollow inorganic fibers.

In one embodiment, the method comprises topically applying a composition comprising 0.1 to 30% by weight of an organic fibrous pigment having an average diameter greater than 0.2 microns and an average aspect ratio greater than 1, to provide a cosmetic film on said skin characterized by substantially Lambertian reflection. In one embodiment, the organic fiber comprises one or more types of organic fiber, for example carbon fiber.

In one embodiment, the method comprises topically applying a composition comprising 0.1 to 30% by weight of a mixture of organic fibrous pigments and inorganic fibrous pigments having an average diameter greater than 0.2 microns and an average aspect ratio greater than 1, to provide a cosmetic film on said skin characterized by substantially Lambertian reflection.

In one embodiment, the method comprises topically applying a composition comprising 0.1 to 30% by weight of a coated polymeric fiber having a diameter greater than 0.2 microns and an average aspect ratio greater than 1, to provide a cosmetic film on said skin characterized by substantially Lambertian reflection. The coated polymeric fibers are as described herein, including but not limited to polymeric materials coated with inorganic fibers or inorganic substances.

In any of the foregoing methods, the composition further comprises a coloring agent or pigment.

In any of the foregoing methods, the cosmetic film on said skin is characterized by measuring the CIELAB color space values L*, a* and b*. In certain methods, the change or difference in color space values of the skin covered with a cosmetic film of any of the foregoing compositions compared to the color space values of natural skin is minimized. In certain embodiments, the difference between the sum of L*, a* and b* color space values of the skin covered with a cosmetic film and the sum of L*, a* and b* color space values of natural skin is less than 30%, 25%, 20%, 15%, 10%, 5%, or 2% of the color space values of natural skin.

In certain embodiments, the difference in L* value of skin covered with a cosmetic film of any of the foregoing compositions as compared to natural skin is less than 2%, 3%, 4%, 5%, 6%, 7% or 10%. In a preferred embodiment, the difference in L* is less than 6%, or more preferably, less than 3%. In certain embodiments, the difference in L* value of skin covered with a cosmetic film of any of the foregoing compositions compared to natural skin is in the range of about 0 to 2%, 0 to 3%, 0 to 4%, 0 to 5%, 0 to 6%, 0 to 7% or 0 to 10%. In a preferred embodiment, the difference in L* is in the range of about 0 to 6%, or more preferably, about 0 to 3%.

In certain embodiments, the change in a* value of skin covered with a cosmetic film of any of the foregoing compositions compared to natural skin is less than 20%, 19%, 18%, 17%, 16%, 15%, 14%, 13%, 12%, 11% or 10%. In a preferred embodiment, the difference in a* is less than 18%, or more preferably, less than 16%. In certain embodiments, the difference in a* value of skin covered with a cosmetic film of any of the foregoing compositions compared to natural skin is in the range of about 0 to 20%, 0 to 19%, 0 to 18%, 0 to 17%, 0 to 16%, 0 to 15%, 0 to 14%, 0 to 13%, 0 to 12%, 0 to 11% or 0 to 10%. In a preferred embodiment, the difference in a* is in the range of about 0 to 18%, or more preferably, about 0 to 16%.

In a particular embodiment, the difference in a* as compared to the a* of natural skin, is less by using fibrous pigments with an average diameter greater than 0.2 microns and an average aspect ratio greater than 5 in the methods described herein, than when using non-fibrous pigments or fibrous pigments with an average aspect ratio less than 5.

In certain embodiments, the difference in b* value of skin covered with a cosmetic film of any of the foregoing compositions compared to natural skin is less than 40%, 35%, 34%, 33%, 14%, 13%, 12%, 11% or 10%. In a preferred embodiment, the difference in b* is less than 18%, or more preferably, less than 16%. In certain embodiments, the difference in b* value of skin coated with a cosmetic film of any of the foregoing compositions compared to natural skin is in the range of about 0 to 20%, 0 to 19%, 0 to 18%, 0 to 17%, 0 to 16%, 0 to 15%, 0 to 14%, 0 to 13%, 0 to 12%, 0 to 11% or 0 to 10%. In a preferred embodiment, the difference in b* is in the range of about 0 to 18%, or more preferably, about 0 to 16%.

In certain embodiments, the difference in a* value is less than 18% and the difference in L* value is less than 6% for skin covered with a cosmetic film of any of the foregoing compositions compared to natural skin. In certain subembodiments, the compositions comprise 2-10% by weight fibrous pigments with an average diameter greater than 0.2 microns and an average aspect ratio greater than 5.

In one embodiment, the compositions comprising the fibrous pigment of the present invention are characterized by a difference of less than 10% in L* across a range of angles of −20° to 130° from specular at an incident angle of less than 60° as compared to the L* of natural skin at each point.

In one embodiment, the coating of the composition on skin is about a 0.3 mils thick film. In certain embodiments, the coating of the composition on skin is less than about a 0.3 mils thick film.

In one embodiment, the composition is characterized by a diffuse transmittance of at least 35 and reflectance value of less than 30 on a 0.3 mils thick film.

A person skilled in the art can select the appropriate presentation form, and also the method of preparing it, on the basis of general knowledge, taking into account the nature of the constituents used and the intended use of the composition.

The composition useful for the methods of the present invention are generally prepared by conventional methods such as are known in the art of making topical compositions. Such methods typically involve mixing of the ingredients in one or more steps to a relatively uniform state, with or without heating, cooling, application of vacuum, and the like.

In another embodiment the composition can be employed as it is and can itself constitute a skin care or make-up composition, lotion, a make-up base, a top-coat and other cosmetic products. The formulations may be anti-aging, restructuring, stimulating, free-radical scavenger, antioxidant, anti-acne, calming, anti-neuromediator, anti-Substance P anti-allergic, pain relief, anti-stress, anti-wrinkle, pro-firmness, pro-elasticity, cicatrizing, toning, tensioning, slimming, veinotonic, draining, anti-redness, immunomodulatory, lightening or revitalizing formula, or else formula intended to improve the complexion of the skin, to stimulate the cells or to promote the synthesis of the proteins of the skin, such as collagen or keratin.

The formulations having moisturizing and/or restructuring activity on the epidermis which incorporate a fibrous pigment according to the invention may be prepared by the methods conventionally used by those skilled in the art in the cosmetology field or in the dermopharmacy field.

The compositions herein can be used by topically applying to the areas of the skin an effective amount of the compositions. The effective amount can easily be determined by each user.

The composition can be applied for several days, weeks, months or years at any intervals. The compositions are generally applied by light massaging the composition onto the skin. However, the method of application may be any method known in the art and is thus not limited to the aforementioned.

In a particular embodiment, the composition is applied once per day or twice per day. In another embodiment, more than one layer of the composition is applied.

The following examples describe specific aspects of the invention to illustrate the invention and provide a description of the present methods for those skilled in the art. The Examples should not be construed as limiting the invention as the examples merely provide specific methodology useful in the understanding and practice of the invention and its various aspects.

EXAMPLES

It is to be understood by those skilled in the art that while certain preferred and alternative embodiments of the invention have been set forth for purposes of disclosing the invention, modification to the disclosed embodiments can occur.

Example 1

Color Space Comparison of Compositions Including 5% by Weight Fibrous Pigment or 5% by Weight Spherical Microfine $TiO_2$ Compositions of 5% by weight fibrous pigment ($TiO_2$ nanofiber as produced by known literature techniques, for example J. Y. Park and S. S. Kim, *Metals and Materials International*, Vol 15(1), pp. 95-99 (2009)) or 5% by weight microfine $TiO_2$ (Color Techniques Inc., Micro Titanium Dioxide USP) in a base of 50% by weight Velvasil 7-4 (Momentive Performance Polymers), 30% TMF, 20% Dow Corning Fluid (100,000 cst fluid) were prepared. Both samples were applied in controlled dosage to the forearm. The microfine $TiO_2$ appeared ashy and chalky whereas the $TiO_2$ fiber was perceived as natural. Both were perceived as lightening the complexion of the skin. Changes in CIE L*, a*, b* values in Velvasil 7-4 base drawdowns of 5% fibrous pigment and 5% microfine $TiO_2$ were quantified (data shown in FIG. 1.) Generally, the compositions with $TiO_2$ fibers provide less shift in the CIE L*, a*, b* values from the base values than those with spherical microfine $TiO_2$. Compositions that minimize deviations from CIE L*, a*, b* values of natural skin will appear more natural than those with larger shifts CIE L*, a*, b* values.

Example 2

Color Space Values of Whitening Creams with 5% Fibrous Pigment or 5% Spherical $TiO_2$ on Skin CIE L, a, b values of natural skin of various subjects was recorded before and after topical application of a whitening cream comprising 5% by weight fibrous pigment ($TiO_2$ nanofiber as above) or 5% by weight microfine $TiO_2$ (Kowett Titanium Dioxide) (see Table 1.) CIE L*, a* and b* values are reported relative to illuminant standard D65.

TABLE 1

| Subj. | Arm | L* before | a* before | b* before | Treatment | L* after | a* after | b* after | ΔL* | Δa* | Δb* |
|---|---|---|---|---|---|---|---|---|---|---|---|
| 1 | left | 53.3 | 11.0 | 22.2 | None | 53.31 | 10.93 | 22.68 | 0.1 | −0.1 | 0.5 |
|   | left | 50.5 | 10.1 | 21.0 | TiO$_2$ Fiber | 51.94 | 9.01 | 15.75 | 1.5 | −1.1 | −5.3 |
|   | right | 50.5 | 10.9 | 21.3 | Spherical TiO$_2$ | 55.17 | 8.63 | 13.42 | 4.6 | −2.2 | −7.9 |
| 2 | left | 58.9 | 10.2 | 20.9 | None | 59.13 | 10.4 | 19.64 | 0.2 | 0.2 | −1.2 |
|   | left | 58.4 | 10.1 | 20.7 | TiO$_2$ Fiber | 59.61 | 9.76 | 14.95 | 1.0 | −1.1 | −6.8 |
|   | left | 56.6 | 11.8 | 20.1 | Spherical TiO$_2$ | 59.9 | 9.63 | 14.68 | 3.3 | −2.2 | −5.4 |
| 3 | left | 65.4 | 9.4 | 18.9 | None | 64.66 | 7.57 | 17.37 | −0.7 | −1.8 | −1.5 |
|   | left | 64.6 | 8.9 | 18.8 | TiO$_2$ Fiber | 66.94 | 8.24 | 15.87 | 2.3 | −0.6 | −2.9 |
|   | left | 63.9 | 10.6 | 19.1 | Spherical TiO$_2$ | 67.33 | 6.13 | 14.53 | 1.9 | −3.2 | −4.4 |
| 4 | left | 56.3 | 10.9 | 20.3 | None | 55.84 | 10.34 | 19.78 | −0.4 | −0.5 | −0.5 |
|   | left | 56.2 | 11.1 | 20.5 | TiO$_2$ Fiber | 59.29 | 9.41 | 13.91 | 3.1 | −1.7 | −6.6 |
|   | left | 57.6 | 10.9 | 20.8 | Spherical TiO$_2$ | 62.26 | 8.54 | 14.77 | 4.7 | −2.3 | −6.0 |

Figure 2A:
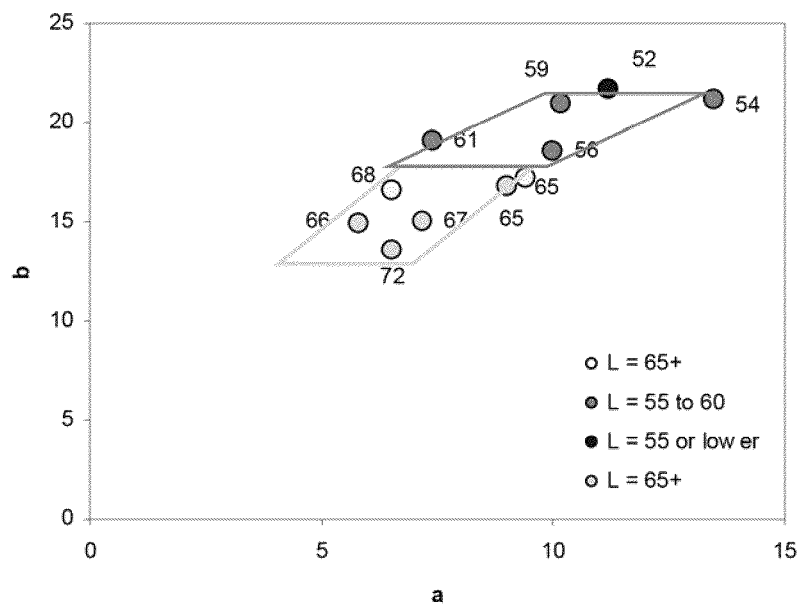
FIG. 2a shows and 2b shows the CIELAB L*, a* and b* values of natural skin before application of a whitening cream.
Figure 2B:
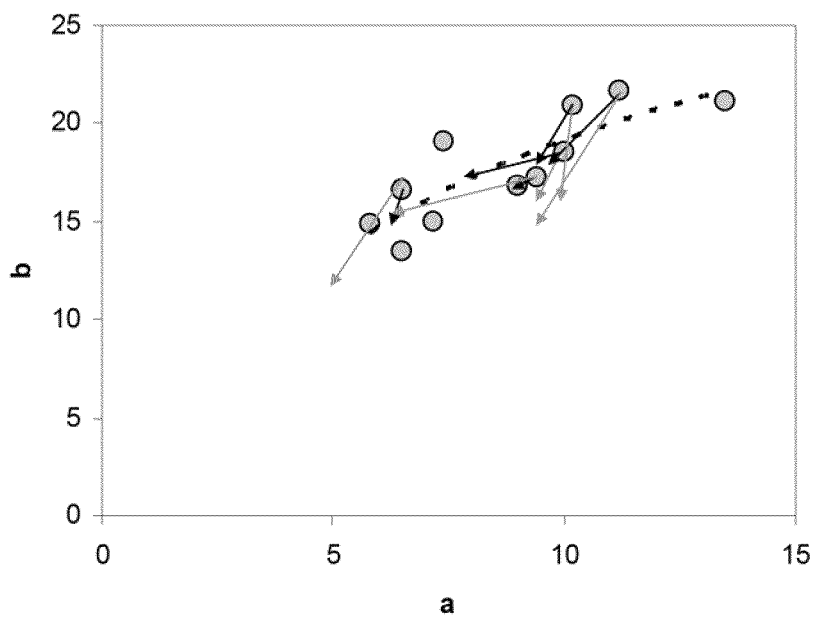
FIG. 2b shows the changes in CIELAB L*, a* and b* values after application of a whitening cream comprising 5% by weight $TiO_2$ fiber (black arrows) or 5% by weight spherical. $TiO_2$ (gray arrows) to skin.

CIE a and b values of natural skin for each individual subject are shown in FIG. 2a. Corresponding CIE L* values are indicated in the chart next to each data point. The shift in CIE L*, a* and b* values for each individual after application of a 5% TiO$_2$ fiber composition (black arrows) or a 5% spherical TiO$_2$ composition (gray arrows) is shown in FIG. 2b.

Example 3

Diffuse Transmission (Soft Focus) and Reflectance Properties of Drawdowns of Fibrous Pigments Compared to Other Soft Focus Materials Compositions comprising 5% by weight of fibrous pigment or other soft focus materials in a base of 50% by weight Velvasil 7-4 (Momentive Performance Polymers), 30% TMF, 20% Dow Corning 200 Fluid were prepared. Diffuse transmittance and reflectance measurements of were obtained for 3 mils thick wet films of each composition. The concentration (% by weight) of the inorganic fibers or particulate materials and the base for each composition and the corresponding diffuse transmittance and reflectance data for each sample is presented in Table 2.

TABLE 2

|  | 1 | 2 | 3 | 4 | 5 | 6 | 7 | 8 | 9 | 10 | 11 |
|---|---|---|---|---|---|---|---|---|---|---|---|
| Nanofiber TiO$_2$ | 5 |  |  |  |  |  |  |  |  |  |  |
| Covalumine TiO$_2$ |  | 5 |  |  |  |  |  |  |  |  |  |
| Nanofiber Alumina |  |  | 5 |  |  |  |  |  |  |  |  |
| Nanofiber SiO$_2$ |  |  |  | 5 |  |  |  |  |  |  |  |
| Unipure White (LC989 AS-EM) |  |  |  |  | 5 |  |  |  |  |  |  |
| Fumed Silica |  |  |  |  |  | 5 |  |  |  |  |  |
| Fumed Alumina |  |  |  |  |  |  | 5 |  |  |  |  |
| Nylon Powder |  |  |  |  |  |  |  | 5 |  |  |  |
| Microfine TiO$_2$ |  |  |  |  |  |  |  |  | 5 |  |  |
| Halloysite |  |  |  |  |  |  |  |  |  | 5 |  |
| Base | 95 | 95 | 95 | 95 | 95 | 95 | 95 | 95 | 95 | 95 | 100 |
| Diffuse Transmittance | 37 | 33 | 38 | 37 | 36 | 45 | 53 | 37 | 36 | 67 | 29 |
| Reflectance | 24 | 31 | 13 | 14 | 40 | 14 | 14 | 13 | 30 | 13 | 14 |

Example 4

Diffuse Transmission and Reflectance of Composition with Halloysite Or Cellulose Beads or Mixture of Halloysite and Cellulose Beads Diffuse transmission, reflectance and total transmission measurements were obtained for compositions comprising 10% by weight cellulose beads, 10% by weight Halloysite or 5% by weight cellulose beads and 5% by weight Halloysite. The results are shown in Table 3.

TABLE 3

|  | Diffuse Transmission | Reflection | Total Transmission | Fraction Diffuse Transmission |
|---|---|---|---|---|
| 10% cellulose beads | 67 | 13 | 73 | 92 |
| 10% Halloysite | 65 | 15 | 70 | 92 |
| 5% cellulose beads and 5% Halloysite | 64 | 16 | 68 | 93 |

Of the three formulations, the composition comprising 10% Halloysite or 5% by weight cellulose beads and 5% by weight Halloysite was determined to possess improved blurring on hands and face. The composition comprising 5% by weight cellulose beads and 5% by weight Halloysite was determined to provide blurring on hands and face and good feel.

Example 5

Figure 3A:
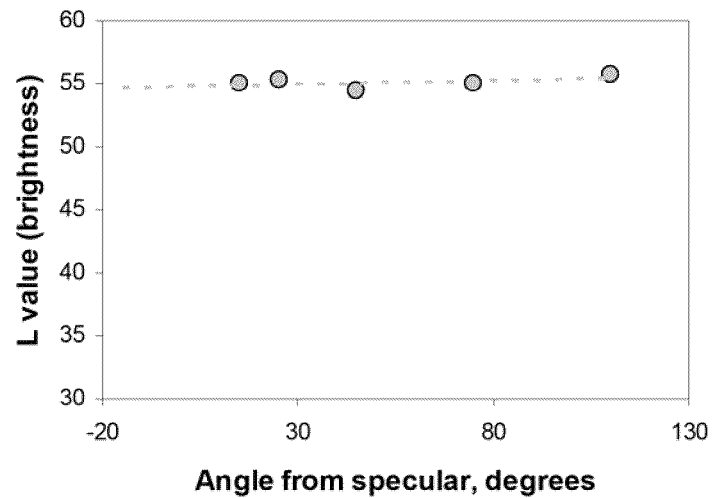
FIGS. 3a and 3b show the L* value of natural skin recorded before (FIG. 3a) and after (FIG. 3b) topical application of a skin lotion composition comprising 5% by weight fibrous $TiO_2$ or 5% by weight spherical $TiO_2$ from angles ranging from −20° to 130° from specular.
Figure 3B:
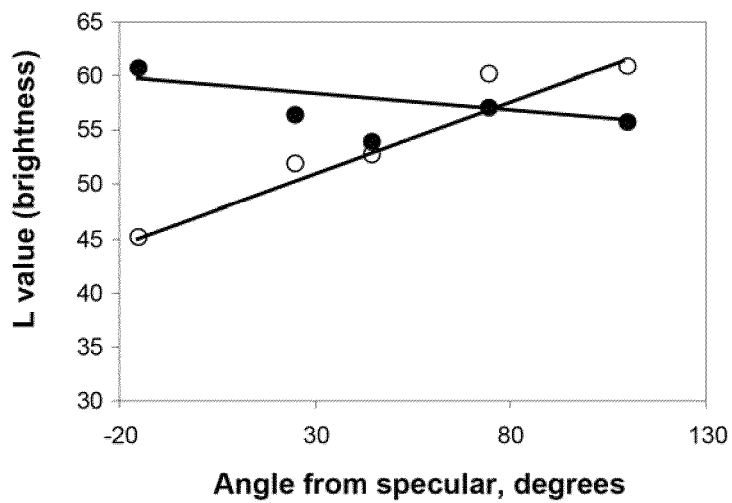

Comparison of Angular Reflectance of Spherical Pigments and Fibrous Pigments The L* value of natural skin was recorded before and after topical application of a skin lotion composition comprising 5% by weight fibrous pigment (TiO$_2$ nanofiber) or 5% by weight spherical TiO$_2$ from several angles ranging from −20° to 130° from specular. L* values for natural skin for various angles is shown in FIG. 3a. L* values for the compositions comprising fibrous TiO$_2$ (black dots) or spherical TiO$_2$ (white dots) for various angles is shown in FIG. 3b. CIE L* values are reported relative to illuminant standard D65. The incident angle was 45°.

The angular reflection of natural skin was observed to be approximately flat (Lambertian reflectance). In particular, skin has a close to Lambertian reflection profile at incident angles of less than 60°. The data demonstrates that the composition containing fibrous TiO$_2$ provides close to Lambertian reflection profile or a natural skin reflection profile, while the composition containing spherical TiO$_2$ possesses a high angular dependence of reflected light and caused the skin to appear ashy or grayish. Skin to which the composition comprising the fibrous pigment (TiO$_2$ nanofiber) was applied was determined to have a substantially flat angular dependence or Lambertian profile and appeared more like the natural skin. The composition with fibrous pigment was perceived as having a whitening effect with more naturalness.

Small panel data regarding the naturalness of the two compositions is provided in Table 4.

TABLE 4

|  | 5% spherical | 5% fibrous |
|---|---|---|
| Does your forearm appear lighter? | 6 - yes | 6 - yes |
| Which cream looks lighter? Chose one. | 2 - yes | 4 - yes |
| Does skin for applied area look natural? Chose one. | 1 - yes | 5 - yes |

Example 6

Effect of Diameter of the Fibrous Pigment on Color Space Values (CIE a* and b* Values)

Figure 4A:
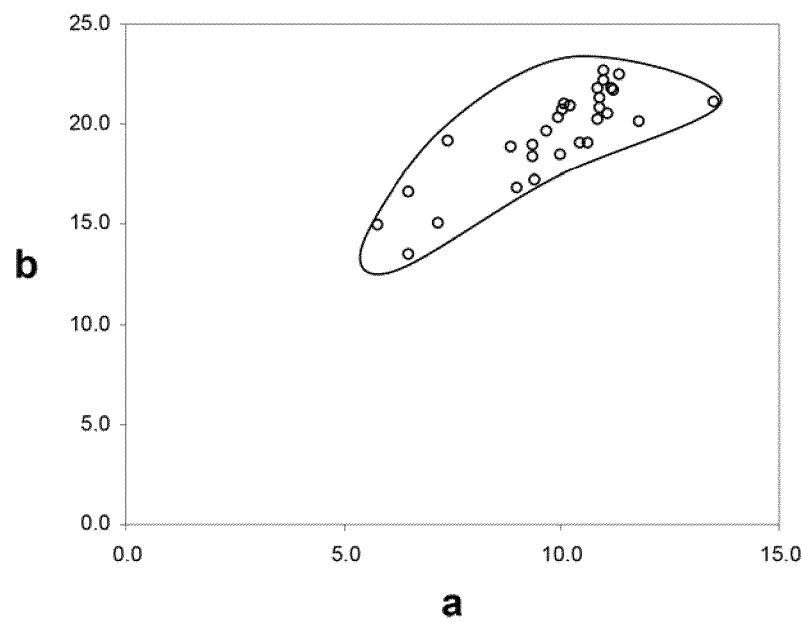
FIG. 4a shows a zone of CIE a* and b* values which characterize natural skin tones.

CIE a* and b* values of natural skin of people with various skin tones were measured. The results, shown in FIG. 4a, define a zone of a-b space values which can be considered natural.

Figure 4B:
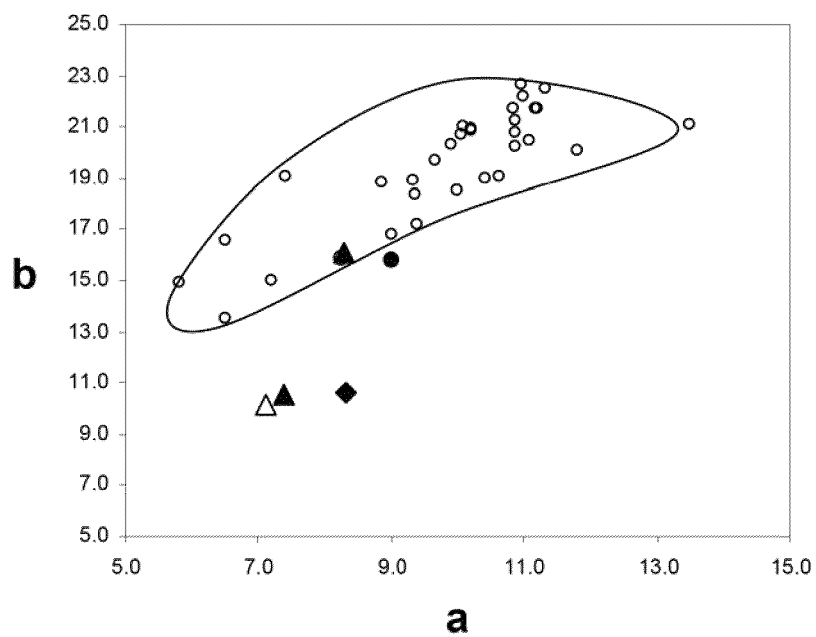
FIG. 4b shows CIE a* and b* values obtained after application of compositions comprising a silicone base and 5% by weight $TiO_2$ fiber of varying sizes in the range of 10 nm to 300 nm.

Compositions comprising a silicone base and 5% by weight TiO$_2$ fiber of varying sizes in the range of 10 nm to 300 nm were prepared. CIE a* and b* values of natural skin of people with various skin tones were measured. The results are shown in FIG. 4b. The following materials were tested at 5% (w/w) loading:

1. TiO$_2$ (fiber, 300 nm diameter, anatase phase) [black circle]
2. TiO$_2$ (fiber, 270 nm diameter, rutile phase) [black triangle]
3. TiO$_2$ (fiber, 200 nm diameter, rutile phase) [black square]
4. TiO$_2$ (fiber, 100 nm diameter, rutile phase) [hollow black square]
5. TiO$_2$ (fiber, 10 nm diameter, rutile phase) [black diamond].

Representative data points are shown for a person with a color tone that is centrally located within the color space. The color of the TiO$_2$ fibers was found to correlate with size. In particular, fibers with diameters of 200 nm and less show a color tone outside of the natural zone. Small panel data regarding the naturalness of the two compositions is provided in Table 5.

TABLE 5

|  | 10 nm | 100 nm | 200 nm | 270 nm | 300 nm |
|---|---|---|---|---|---|
| Does skin look lighter? | 4 - Yes | 5 - Yes | 5 - Yes | 5 - Yes | 5 - Yes |
| Does skin look natural? | 5 - No | 5 - No | 5 - No | 5 - Yes | 5 - Yes |

All 5 panelists reported that the 10, 100 and 200 nm diameter samples looked bluish and un-natural. Compositions containing fibers >200 nm were found to provide a natural looking tone.

Example 7

Figure 5:
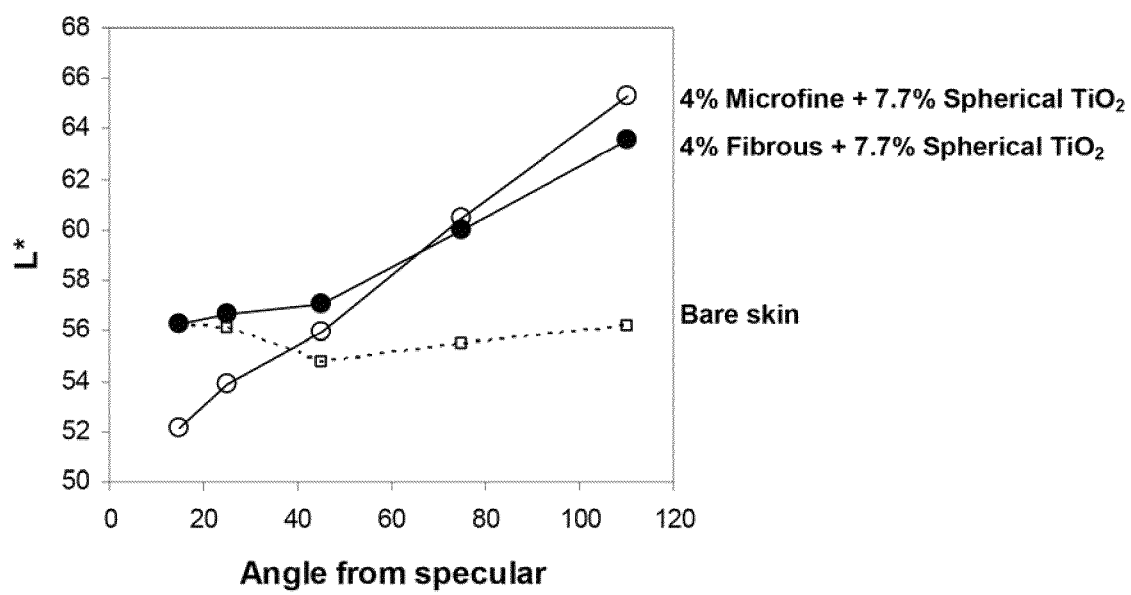
FIG. 5 shows the L* value of natural skin recorded before and after topical application of a high coverage foundation composition comprising 5% by weight fibrous $TiO_2$ or 5% by weight spherical $TiO_2$ from angles ranging from −20° to 130° from specular.

Comparison of Angular Reflectance of Spherical Pigments and Fibrous TiO$_2$ in a High Coverage Liquid Foundation The L* value of natural skin was recorded before and after topical application of a high coverage foundation comprising 4% by weight fibrous pigment (TiO$_2$ nanofiber) and 7.7% Spherical TiO$_2$ (U.S. Cosmetics Inc. ST-PEG/MOD-TAS-77891) or 4% by weight microfine TiO$_2$ (Color Techniques Inc., Micro Titanium Dioxide USP) and 7.7% Spherical TiO$_2$ (U.S. Cosmetics Inc. ST-PEG/MOD-TAS-77891) from several angles ranging from −20° to 130° from specular. L* values for natural skin (white squares) for various angles is shown in FIG. 5. L* values for the compositions comprising fibrous and spherical TiO$_2$ (solid black dots) or microfine and spherical TiO$_2$ (white dots) for various angles is shown in FIG. 5. CIE L* values are reported relative to illuminant standard D65. The incident angle was 45°.

The angular reflection of natural skin was observed to be approximately flat. The data demonstrates that the composition containing fibrous TiO$_2$ provides a scattering profile closer to natural skin, while the composition containing spherical and microfine TiO$_2$ possesses a high angular dependence of reflected light and caused the skin to appear ashy. Skin to which the composition comprising the fibrous pigment (TiO$_2$ nanofiber) was applied was determined to have a substantially flat angular dependence or Lambertian profile and appeared more like the natural skin. The composition with fibrous pigment was perceived as having a more naturalness.

Small panel data regarding the naturalness of the two compositions is provided in Table 6.

|  | 6% Fibrous + 6% Spherical TiO$_2$ | 6% Microfine + 6% Spherical TiO$_2$ |
|---|---|---|
| Which appears most natural? | 4 - yes | 1 - yes |

The invention claimed is:

1. A method of imparting a pigmented film on skin comprising topically applying a composition comprising 0.1 to 30% by weight of a fibrous pigment having an average diameter greater than 0.2 microns and an average aspect ratio greater than 5 and from 0.1 to 30% of a coloring agent, selected from pigments, lakes, and dyes, to provide a cosmetic film on said skin characterized in that the appearance of the skin is more natural than a film provided by an otherwise identical composition wherein the fibrous pigment has an average aspect ratio of less than 5, wherein the fibrous pigment having an average diameter greater than 0.2 microns and an average aspect ratio greater than 5 comprises a metal oxide.

2. The method of claim 1, wherein the composition is a colored make-up composition.

3. The method of claim 2, wherein the colored make-up composition is foundation.

4. The method of claim 1, wherein the composition comprises iron oxide.

5. The method of claim 1, wherein the composition comprises one or more sunscreen agents.

6. The method of claim 1, wherein the composition comprises one or more film-forming agents.

7. A method of imparting a pigmented film on skin comprising topically applying a composition comprising 0.1 to 30% by weight of a fibrous pigment having an average diameter greater than 0.2 microns and an average aspect ratio greater than 5 and from 0.1 to 30% of a coloring agent, selected from pigments and dyes, to provide a cosmetic film on said skin characterized in that the appearance of the skin is more natural than a film provided by an otherwise identical composition wherein the fibrous pigment has an average aspect ratio of less than 5, and wherein the fibrous pigment comprises a metal oxide.

8. The method of claim 7, wherein the fibrous pigment is fibers comprised of a polymeric material and coated with the metal oxide.

9. The method of claim 7, wherein the metal oxide is $TiO_2$, Halloysite, ZnO, or an iron oxide.

10. A method of imparting a pigmented film on skin comprising topically applying a composition comprising 0.1 to 30% by weight of a fibrous pigment having an average diameter greater than 0.2 microns and an average aspect ratio greater than 5 and from 0.1 to 30% of a coloring agent, selected from pigments, lakes, and dyes, to provide a cosmetic film on said skin characterized in that the appearance of the skin is more natural than a film provided by an otherwise identical composition wherein the fibrous pigment has an average aspect ratio of less than 5, wherein the composition is characterized by a diffuse transmittance of at least 35 and reflectance value of less than 30 on a 0.3 mils thick film, and wherein the fibrous pigment comprises a metal oxide.

11. The method of claim 10, wherein the fibrous pigment is fibers comprised of a polymeric material and coated with the metal oxide.

12. The method of claim 10, wherein the metal oxide is $TiO_2$, Halloysite, ZnO, or an iron oxide.

13. The method of claim 1, wherein the fibrous pigment is fibers comprised of a polymeric material and coated with the metal oxide.

14. The method of claim 1, wherein the metal oxide is $TiO_2$, Halloysite, ZnO, or an iron oxide.

15. The method of claim 1, wherein the fibrous pigment is Halloysite or $TiO_2$ nanofiber.

16. The method of claim 1, wherein the fibrous pigment is fibers with asperities.

17. The method of claim 1, wherein the cosmetic film on the skin is characterized by substantially Lambertian reflection.

* * * * *